United States Patent [19]

Derechinsky

[11] 4,367,746

[45] Jan. 11, 1983

[54] CLIP-HOLDER INSTRUMENT FOR CLIPPING BLOOD VESSELS

[76] Inventor: Victor E. Derechinsky, Sarmiento St. No. 2176, Buenos Aires, Argentina

[21] Appl. No.: 214,105

[22] Filed: Dec. 8, 1980

[30] Foreign Application Priority Data

Dec. 11, 1979 [AR] Argentina ............................ 279236

[51] Int. Cl.³ .......................................... A61B 17/12
[52] U.S. Cl. .................................. 128/325; 29/243.56
[58] Field of Search ...................... 128/325; 29/243.56

[56] References Cited

U.S. PATENT DOCUMENTS

| 3,958,576 | 5/1976 | Komiya ........................... 29/243.56 |
| 4,169,476 | 10/1979 | Hiltebrandt ........................ 128/325 |
| 4,241,734 | 12/1980 | Kandel et al. ...................... 128/325 |
| 4,246,903 | 1/1981 | Larkin ................................ 128/325 |
| 4,304,236 | 12/1981 | Conta et al. ........................ 128/325 |

Primary Examiner—Kyle L. Howell
Assistant Examiner—Daniel P. Burke
Attorney, Agent, or Firm—Allegretti, Newitt, Witcoff & McAndrews

[57] ABSTRACT

An instrument and method for clipping blood vessels are disclosed. The new surgical tool disclosed is particularly adequate to place clips of alpha configuration ending in "V" on brain blood vessels. The invention enables a surgeon to have a free field of vision of the area and the blood vessel to be clipped as well as the clip carried by the instrument.

8 Claims, 8 Drawing Figures

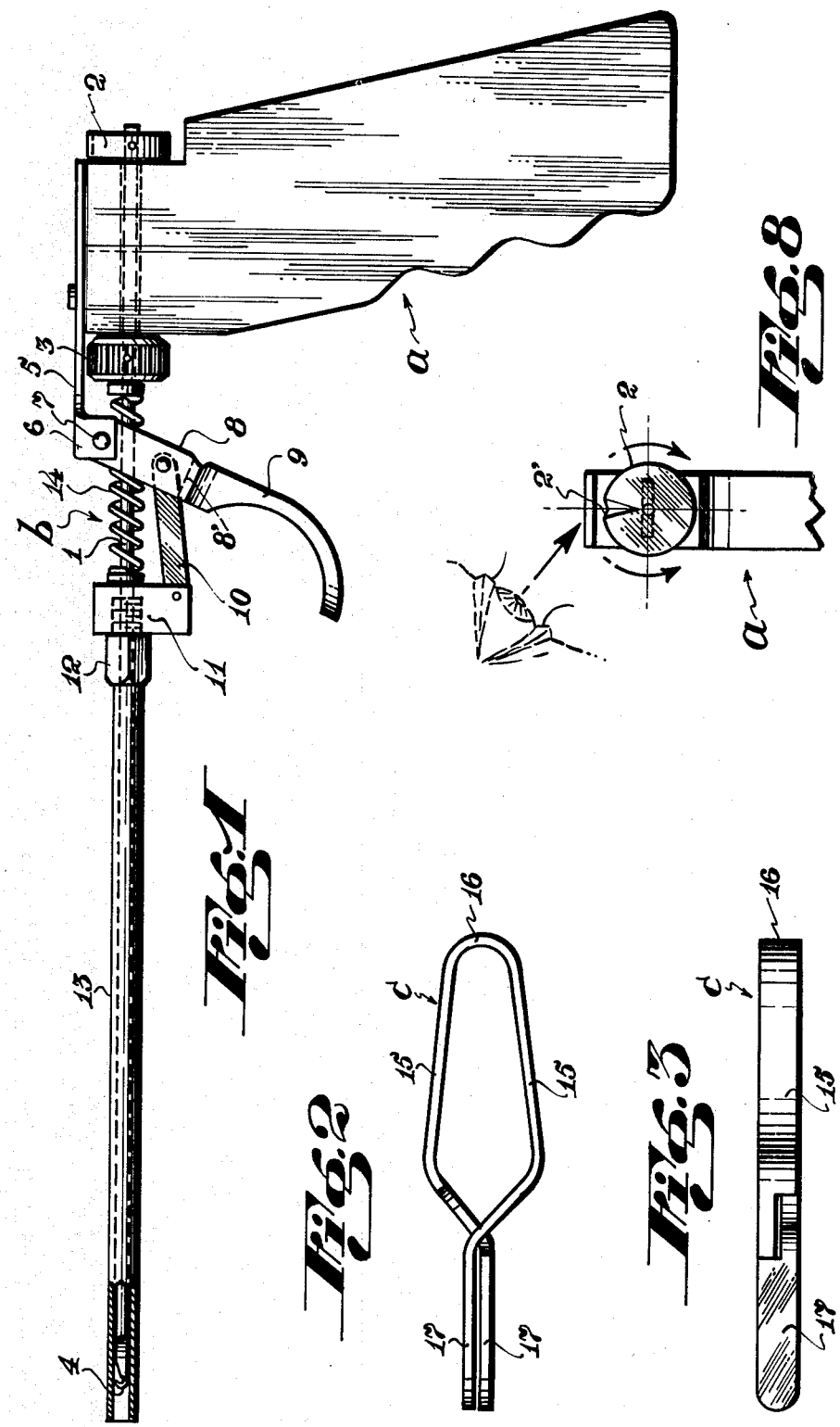

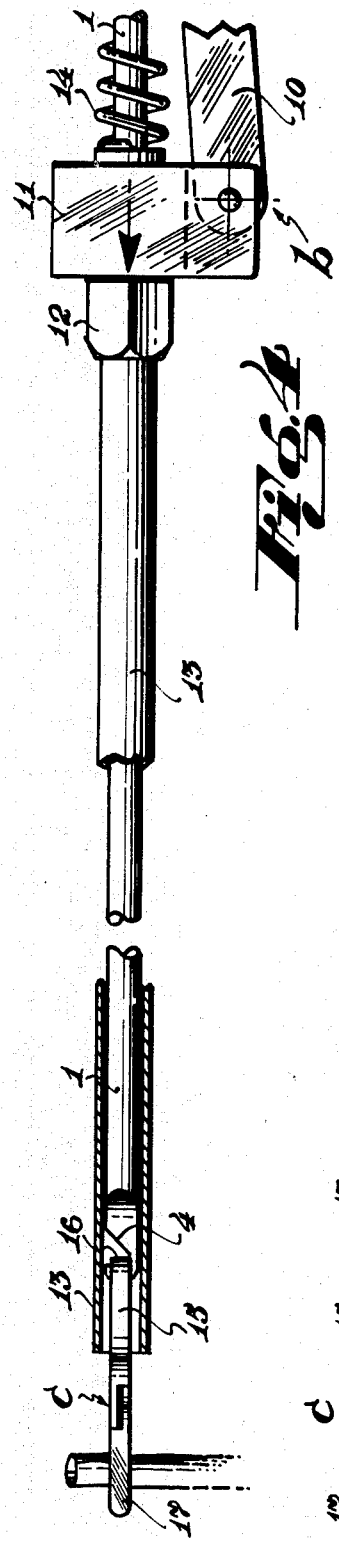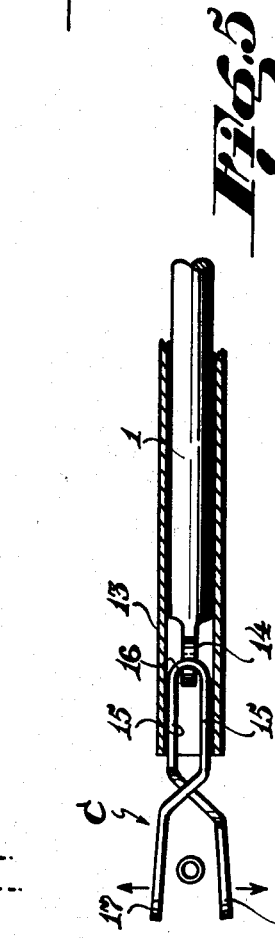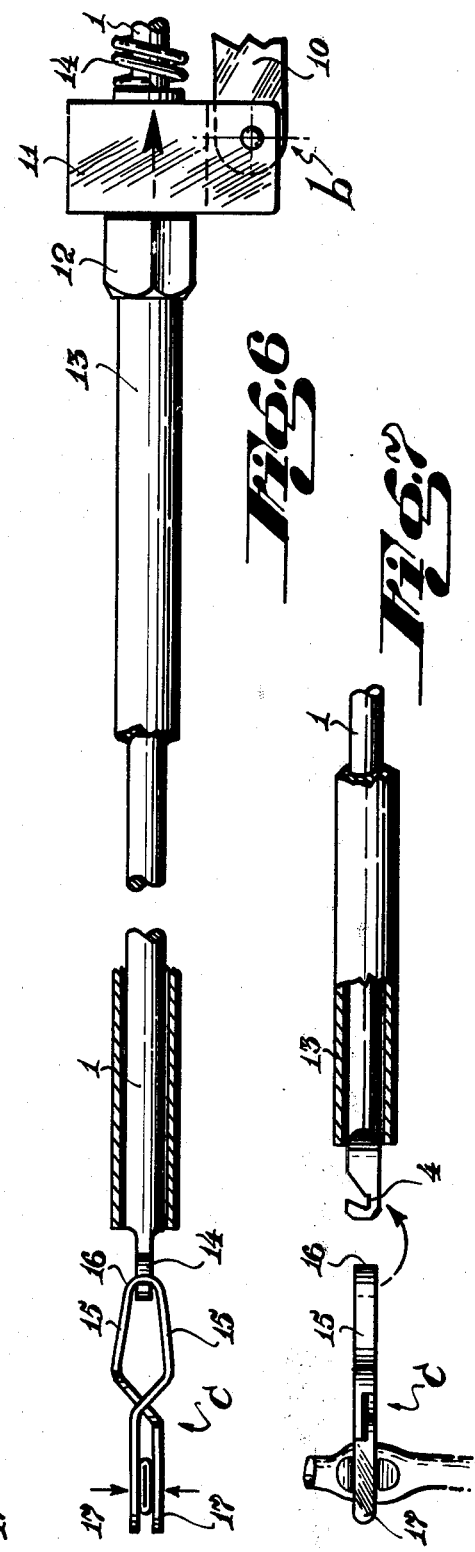

CLIP-HOLDER INSTRUMENT FOR CLIPPING BLOOD VESSELS

BACKGROUND AND SUMMARY OF THE INVENTION

The present invention relates to a clip-holder instrument for "clipping" blood vessels, and especially to a new surgical tool particularly adequate to place clips, of alpha configuration ending in "V", on brain blood vessels.

The clip-holder pliers used at present have several drawbacks that in view of the particular and delicate task for which they are used, such as in neurosurgery, make the surgeon's task especially difficult when he requires the best working conditions and, more importantly, have an operating field of vision free from obstacles.

In the above mentioned pliers the clip is closed. This means that, when the pliers are open the clip is closed, to open it and place it in position, the pliers must be closed, the force to be applied varying according to the type of pliers used. Some of them (such as those known as the Mayfield and Scoville pliers), when they are closed for the clip to open, are unsafe and the clip may fall out or change its position. In the pliers called Yassagil the mechanism is similar with the added disadvantage that it is difficult to unfasten the clip from the pliers when it is placed.

The Olivecrona clip-holder pliers, at present obsolete, carried the clip open. The drawback in such a configuration consisted in the fact that the fastening of the clip in its position on the blood vessel was obtained by the strength of the surgeon's hand and not through the elasticity of the clip. As a consequence of the foregoing, deficient fastening of the clip on the blood vessel could occur or, alternatively, excessive pressure could be created that, in the case of carelessness, could section the aneurysmatic neck.

Another important disadvantage of the above mentioned pliers is that they obstruct the surgeon's field of vision, as the jaws of the pliers are larger than the clip to be placed. It must be borne in mind that the surgeon works within the encephalic mass, with a microscope. It sometimes happens that it is not possible to verify if the clip is correctly placed until it is released. If it is not in the correct position, which frequently happens, the clip must be withdrawn and replaced in the correct position.

Another disadvantage of the above mentioned pliers is that it is difficult to withdraw a clip that has been incorrectly placed, added to the fact that it is not possible to turn it in the pliers when the operation so requires. This obliges the surgeon to turn his hand according to the position of the clip, which is complicated by the above mentioned drawback that the pliers obstruct the surgeon's field of vision for placing the clip.

The present instrument of the invention eliminates all these disadvantages and constitutes a very practical and efficient tool.

One of the prinicpal advantages of the present invention is that it provides an instrument that enables the surgeon to have a free field of vision all the time of the area and the blood vessel to be "clipped" as well as the clip carried by the instrument.

Another advantage is that, in an inoperative position the instrument carries the clip open, but it can also be carried in a closed position by means of a slight pressure of the surgeon's hand. In a preferred embodiment of the present invention, the clip is carried within a tube, therefore the possibility that the clip may fall out of the tube or modify its position is eliminated.

Further advantages are that the clip can be carried in the instrument and that its rotation can be controlled with the same hand that holds it, thus sparing the operator from having to turn his hand in order to rotate the clip.

It is also very important to point out that the clip is easily unfastened from the instrument and that it can also be withdrawn without any difficulty. Although the instrument requires pressure to release the clip, the clip closes on the blood vessel due to its own elasticity, and the pressure of the hand is exercised on a lever that is similar to the trigger of a firearm and is easily operated. The instrument forms a grip handle that provides ample safety.

Other advantages and characteristics of the invention may be observed in the course of the description of the preferred embodiment of the present invention.

BRIEF DESCRIPTION OF THE DRAWINGS

For better clarity and understanding the invention is described in further detail with reference to the accompanying drawings that illustrate the clip-holder instrument for "clipping" blood vessels of the invention, in its preferred embodiments, all of the foregoing as a non-limiting example of its scope, in which:

FIG. 1 is an elevated side view of the clip-holder instrument of the invention in which shows the assembly characteristics of the invention. The figure shows the rod in dashes, the end of said rod forming the clamp and release means of the clip joined to the end portion of the tube that is displaceably assembled on the rod.

FIG. 2 is a view of the clip in alpha configuration ending in "V", that is adequate for the instrument of the invention.

FIG. 3 is a view of the clip of FIG. 2 rotating in a right angle in relation to the view of FIG. 2.

FIG. 4 is a partial view of the instrument carrying on its end the open clip as it is brought up to the vessel to be "clipped". In FIG. 4 the arrow points to the normal position of the instrument with the casing tube of the rod extended on the terminal of the instrument in response to the tension of the expansion spring operating on said tube.

FIG. 5 is a view of the operative end of the instrument with a 90° rotation with respect to the view of FIG. 4.

FIG. 5 shows how the tube, in which the clip is partially housed, maintains pressure on the "V" portion of the clip having its prehensile portion open, ready to be placed.

FIG. 6 is a view similar to FIG. 5 that shows that by operating the lever that controls the return displacement of the tube, overcoming the tension of the expansion spring, said tube shows the end of the rod that holds the clip and the elasticity of the clip released from said tube, thereby making the prehensile portion of the clip close on the vessel, as is shown with arrows in said figure.

FIG. 7 is a view that shows how, when the clip is in the position mentioned in FIG. 6, the terminal of the rod is unhooked, thus ending the operation and, finally:

FIG. 8 is a partial view that shows the top end portion of the instrument with the knob fixed on the rear terminal of the rod that has a visual guide of the angular position of the clip placed on the opposite terminal of said rod.

In the different figures the same reference numbers show similar or corresponding parts, indicating with letters the assembly of several elements.

DESCRIPTION OF THE PREFERRED EMBODIMENTS

As may be observed from the drawings, the clip-holder instrument for "clipping" blood vessels of the invention comprises a grip handle a similar to that of a pistol, the operating mechanism b being assembled on the top portion of the instrument.

The upper portion of said grip handle a is passed through by the rear portion of a rod 1 that is free to rotate and has a fixed rear knob or disk 2 and, facing the handle a, an operating knob 3. The opposite terminal of said rod 1 that is rectilinear, forms a hook 4. In FIG. 1, in which rod 1 is round, the above mentioned terminal on which hook 4 is formed is flat for better safety.

On the top portion of the grip handle a a support piece 6 is fixed that projects in front of same forming a pair of branches 6, turned downward, between which a lever 8 is articulated in 7 the power arm of which has the form of a trigger for a better operation, as may be observed in FIG. 1.

The articulated portion of lever 8 has a middle longitudinal groove (not shown in the drawings) on which the end of an arm 10 is articulated, the opposite end of which is connected to a member 11 on which is fixed, by means of a nut 12, a rectilinear tube 13 longitudinally displaceable on rod 1.

Between member 11, that is joined with tube 13 and the front operation knob 3 that is joined with rod 1, is mounted around rod 1 an expansion spring 14.

Said spring 14 operates on member 11 pushing member 11 outward with tube 13, that is to say, tending to separate member 11 from the grip handle a that in an extended position, the free end of said tube 13 comes over the top of hook 4 of the terminal of rod 1 that remains housed within tube 13, as shown in FIGS. 1, 4 and 5.

By pressing arm 9 of lever 8, breaking the tension of spring 14, said lever 8 by means of an arm 10 displaces member 11 toward the rear and tube 13 joined thereto such that in its axial backward motion the free end of hook 4 is shown (FIG. 6).

The outward displacement of member 11 with tube 13 is limited by the support base 8' of the longitudinal groove of lever 8, on which arm 10 is articulated, against said arm—as may be observed in FIG. 1 where said base 8' is shown with dashes—said support constituting the butt of the extension position of spring 14.

The operation knob 3 that controls the rotation of rod 1 with which it is joined, is supported against a ring or annular member of a material such as "teflon" that inserted in the grip handle a decreases the friction of said knob 3, allowing a smoother operation. Said member is not shown in the drawings as it refers to an accessory technical resource. As it may be assumed, the angular displacement of rod 1 may also be operated by means of the back member 2, but in this case the operation becomes difficult to handle with the same hand that holds the instrument. On said member 2 guide 2' is located to obtain an easier visualization of the angular position of rod 1 and, also, that of clip c carried toward the position to place the clip c.

The instrument is particularly adequate to hold and place the clips c of alpha configuration and ending in "V", such as that illustrated in FIGS. 2 and 3.

The clips c have rear branches 15 that are divergent starting from a rounded peak 16 with elastic tension. The branches 15 are intercrossed and end in substantially straight branches 17 that define the prehensile portion of the clip c. The facing portions of said branches 17 have means capable of preventing the sliding of the blood vessel held between the branches 17. The opening of clip c is obtained by the compression of the divergent branches 15, as shown in FIG. 5, thus separating the prehensile branches 17. The release of the divergent arms by means of the elastic tension proper of the branches 15 originated by the rounded peak 16 tends to abutt the branches 17 that press against the blood vessel held between the branches 17 (FIG. 6).

The operation of the instrument is clearly understood from the above mentioned description and drawings. In order to take clip c, one holding the instrument (that is designed to place the middle, ring and little fingers of the hand in the front depressions of the grip handle a leaving the forefinger free to press the power arm 9 of lever 8) presses by means of arm 10 after said arm 9 in the shape of a trigger, in such way that the mechanism b retracts the member 11, with its connected tube 13, against the tension of expansion spring 14, until said movement of the tube 13 uncovers hook 4 of the terminal of rod 1, as is shown in FIG. 6.

Clip c is hooked to said terminal 4 by its rounded peak 16. When clip c is hooked, arm 9 of the lever 8 is released and spring 14 displaces member 11 together with tube 13 to the outward position (FIG. 4). When hook 4 enters in the free end portion of tube 13, the walls of the tube 13 of a smaller internal diameter than the opening determined by the divergent branches 15 of said clip c, elastically compress the branches 15 that enter within the tube originating the separation of the prehensile branches 17 (FIG. 5), thus the clip c remains in the open position and the assembly is in condition to be used. If it is desired to advance with clip c closed, it is sufficient to slightly press arm 9 of lever 8 to partially retract tube 13 until, by releasing the pressure on branches 15 observed on the open end of the tube, their elasticity causes the branches 17 to close. In any of those two forms of advance, clip c is maintained perfectly secure at the end of the instrument as hook 4, that still does not project from tube 13, which retains it in position.

If the operator wishes to rotate clip c, the angular position of which is shown with guide 2' of the rear member 2 connected with rod 1, it is sufficient to press with the thumb of the same hand on knob 3 that by angularly displacing rod 1 effects the same movement on clip c held by hook 4 on the terminal of rod 1. The surface of said knob 3 is knurled or supplied with a similar treatment in order to obtain adherence without slipping.

Thus the instrument can be taken up to the blood vessel to be "clipped", either with clip c to be opened on the placing position (for which it is enough to stop pressing lever 8), or directly opened without pressing lever 8.

As illustrated in FIGS. 4 and 5, the surgeon has an ample field of vision of the projecting end of clip c, that facilitates its placing in the desired position. When the clip is placed, the surgeon presses arm 9 of lever 8 to retract tube 13, until hook 4 of rod 1 projects outward at the end of tube 13 (FIG. 6), thereby decompressing rear branches 15 of clip c that are separated and thus joining the prehensile branches 17 that close on the blood vessel, as shown with arrows in FIG. 6.

When the foregoing operation is effected, the terminal 4 is unhooked (FIG. 7) and the instrument may be withdrawn leaving clip c in position. In the event of wishing to withdraw the clip, the above mentioned operation is reversed.

The mechanism b is effected as illustrated in order to decrease the pressure required on arm 9 when arm 9 must be operated, but lever 8 may be also formed in such way as to operate directly on member 11 (or similar) connected with tube 13; or in an adequate configuration to obtain a similar result.

The arrangement of tube 13 fixed to member 11 by means of nut 12 has the objective of being able to disassemble the arrangement for a comfortable and effective cleaning of the instrument.

It is doubtless that in putting the present invention into practice some modifications may be introduced by those skilled in the art as regards certain details, without departing from the basic principles of the present invention which are clearly specified in the following claims.

Having thus especially described and determined the nature of the present invention and the form in which same has been put in practice, I hereby claim the following as my property and exclusive right:

1. A clip-holder instrument for clipping blood vessels comprising, in combination:
    (a) a grip handle, said grip handle having an upper portion and a bottom portion, said bottom portion being a pistol butt-shaped member;
    (b) operating means for operating said grip handle, said operating means being assembled on said upper portion of said grip handle;
    (c) a clip;
    (d) a rod and tube assembly means for clamping and releasing said clip, having a rod, said rod having a front portion and a rear portion, said rear portion passing through said upper portion of said grip handle, said front portion forming a hooking means for hooking said clip, said rod being freely rotatable and having an operation knob joined on said rear portion of said rod opposite said grip handle, said operation knob controlling the rotation of said rod; and
    (e) lever means and a retraction member for operating said rod and tube assembly, said lever means having a power arm, said power arm being a trigger-shaped member, said lever means extending from said upper portion of said grip handle and being connected to said retraction means.

2. A clip-holder instrument for clipping blood vessels as claimed in claim 1, wherein said clip is a clip of alpha configuration ending in "V".

3. A clip holder instrument for clipping blood vessels as claimed in claim 1, wherein said rod has an angular position and a guiding means thereon, said guiding means facilitating visualization of said angular position of said rod as said rod carries said clip to the position for the placement of said clip.

4. A clip-holder instrument for clipping blood vessels as claimed in claim 1, wherein said rod has a rectilinear tube displaceable lengthwise thereon a retraction member connected to said lever means and said tube and an expansion spring mounted around said rod for biasing said retraction member, said tube being joined to said retraction member.

5. A clip-holder instrument for clipping blood vessels as claimed in claim 4, wherein said expansion spring has a tension thereon, said tension being broken by the pressing of said lever means, said lever means displacing said tube and said retraction member in a backward direction with respect to said hooking means, said hooking means thereby being in position for hooking said clip.

6. A method for clipping blood vessels through the utilization of a clip-holder instrument and a clip, which comprises:
    (a) gripping said instrument in the middle, ring and little fingers of the hand, said instrument having a rod and a lever means thereon, said lever means having a power arm, said rod having a terminal, said terminal including a hooking means for hooking a clip, said rod having a tube displaceable thereon, said tube being displaceable from an inward position to an outward position and having a retraction member joined thereto, said lever means being connected to said retraction means, said retraction member being retractable, said rod having an expansion spring therearound for forwardly biasing said retraction member and said tube, said expansion spring having a tension thereon;
    (b) pressing said power arm of said lever means, thereby retracting said retraction member and said tube joined thereto against said tension of said expansion spring;
    (c) uncovering said hooking means of said terminal of said rod;
    (d) hooking said clip to said hooking means, said clip having branches and prehensile branches and being capable of an open configuration and a closed configuration;
    (e) releasing said power arm of said lever means, thereby displacing said member and said tube to an outward position;
    (f) compressing elastically said branches of said clip thereby permitting said clip to remain in an open position;
    (g) maintaining said clip secure at the end of said instrument by means of said hooking means;
    (h) placing said clip at the desired placement position;
    (i) pressing said power arm of said lever means thereby decompressing said branches of said clip and joining said prehensile branches of said clip to enable said prehensile branches to close on said blood vessel;
    (j) unhooking said hooking means from said clip; and,
    (k) withdrawing said instrument from said blood vessel leaving said clip in position on said blood vessel.

7. A method for clipping blood vessels as claimed in claim 6, wherein said clip is a clip of alpha configuration ending in "V".

8. A method for clipping blood vessels as claimed in claim 6, wherein said tube has a free end portion and walls, said branches of said clip being compressed elastically by means of said hooking means entering said free end portion of said tube, causing said walls of said tube to compress said branches thereby separating said prehensile branches of said clip.

* * * * *